(12) United States Patent
Basheer

(10) Patent No.: US 9,068,175 B2
(45) Date of Patent: Jun. 30, 2015

(54) MODIFIED-IMMOBILIZED ENZYMES OF HIGH TOLERANCE TO HYDROPHILIC SUBSTRATES IN ORGANIC MEDIA

(75) Inventor: Sobhi Basheer, Sakhnin (IL)

(73) Assignee: Trans Bio-Diesel Ltd., Shfaram (IL)

( * ) Notice: Subject to any disclaimer, the term of this patent is extended or adjusted under 35 U.S.C. 154(b) by 385 days.

(21) Appl. No.: 12/599,366

(22) PCT Filed: May 7, 2008

(86) PCT No.: PCT/IL2008/000631
§ 371 (c)(1),
(2), (4) Date: Apr. 21, 2010

(87) PCT Pub. No.: WO2008/139455
PCT Pub. Date: Nov. 20, 2008

(65) Prior Publication Data
US 2010/0209982 A1    Aug. 19, 2010

(30) Foreign Application Priority Data
May 9, 2007  (IL) .......................................... 183084

(51) Int. Cl.
| C12N 9/14 | (2006.01) |
| C12N 9/16 | (2006.01) |
| C12N 9/18 | (2006.01) |
| C12N 9/20 | (2006.01) |
| C12P 7/64 | (2006.01) |
| C12N 11/14 | (2006.01) |
| C12N 11/02 | (2006.01) |
| C07H 21/04 | (2006.01) |
| C12P 7/62 | (2006.01) |

(52) U.S. Cl.
CPC .. *C12N 9/20* (2013.01); *C12N 9/16* (2013.01); *C12N 11/02* (2013.01); *C12N 11/14* (2013.01); *C12P 7/62* (2013.01); *C12P 7/649* (2013.01); *Y02E 50/13* (2013.01)

(58) Field of Classification Search
None
See application file for complete search history.

(56) References Cited

U.S. PATENT DOCUMENTS

| 6,042,824 | A | 3/2000 | Khalaf |
| 6,964,944 | B1 | 11/2005 | Callisen et al. |
| 2004/0077816 | A1 | 4/2004 | Brandstadt et al. |
| 2004/0171126 | A1* | 9/2004 | Basheer et al. ............... 435/128 |
| 2005/0026235 | A1 | 2/2005 | Graham |
| 2005/0031657 | A1 | 2/2005 | Gilson et al. |
| 2007/0202207 | A1* | 8/2007 | McClory et al. ............. 424/776 |
| 2008/0268287 | A1 | 10/2008 | Donadio et al. |
| 2010/0035312 | A1 | 2/2010 | Basheer |

FOREIGN PATENT DOCUMENTS

| WO | 9015868 | 12/1990 |
| WO | 99/15689 | 4/1999 |
| WO | 99/33964 | 7/1999 |
| WO | 00/56869 | 9/2000 |
| WO | 00/75295 | 12/2000 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Bayramoglu et al., Food Chemistry, 92:261-268 (2005). "Immobilization of *Candida rugosa* lipase onto spacer-arm attached poly(GMA-HEMA-EGDMA) microspheres."
Palomo et al., Journal of Molecular Catalysis B: Enzymatic 21:201-210 (2003). "Modulation of *Mucor miehei* lipase properties via directed immobilization on different hetero-functional epoxy resins Hydrolytic resolution of (R,S)-2-butyroyl-2-phenylacetic acid."
Pavlenko et al., Russian Journal of Bioorganic Chemistry, 31(6):535-542 (2005). "Effect of chemical modification of lipase on the regulation of its lipolytic activity in reversed micelles."
Shulai, Liu, Chemical Technology Market, No. 4, vol. 26, 2003. Article No. 1009-4725 (2003) 04-0010-0016-05. "Advance in lipase catalysis." English translation.
Katchalski-Katzir, et al. "Eupergit C, a carrier for immobilization of enzymes of industrial potential", J. of Mol. Catalysis B: Enzymatic 10, pp. 157-176, 2000.
Murakami et al., JAOCS, 70(6):571-574 (1993). "Transesterification of oil by fatty acid-modified lipase."
Persson et al., Enzyme and Microbial Technology, 31:833-841 (2002). "Preparation of lipases for use in organic solvents."
Al-Zuhair, Biofuels, Bioprod. Bioref., 1:57-66 (2007). "Production of biodiesel: possibilities and challenges."
Bajaj et al., Journal of Molecular Catalysis B: Enymatics 62:9-14 (2010). "Biodiesel production through lipase catalyzed transesterification: An overview."
Katchalski-Katzir et al., Journal of Molecular Catalysis B: Enzymatic 10:157-176 (2000). "Eupergit C, a carrier for immobilization of enzymes of industrial potential."
Mateo et al., Enzyme and Microbial Technology, 40:1451-1463 (2007). "Improvement of enzyme activity, stability and selectivity via immobilization techniques."
Salis et al., Journal of Molecular Catalysis B: Enzymatic 57:262-269 (2009). "Role of the support surface on the loading and the activity of *Pseudomonas fluorescens* lipase used for biodiesel synthesis."

* cited by examiner

*Primary Examiner* — Iqbal H Chowdhury
(74) *Attorney, Agent, or Firm* — Nixon Peabody LLP; David S. Resnick; Leena H. Karttunen Contarino

(57) ABSTRACT

Disclosed are preparations of modified interfacial enzymes, particularly lipases and phospholipases, immobilized on a solid support, wherein the enzyme is surrounded by hydrophobic microenvironment, thereby protected from deactivation and/or aggregation in the presence of hydrophilic agents, substrates and/or reaction products. The enzyme may be protected by being covalently bonded with lipid groups which coat the enzyme, or by being immobilized or embedded in a hydrophobic solid support. Also disclosed are processes for the preparation of the hydrophobically protected enzymes. The enzymes may be efficiently used in the preparation of biodiesel.

7 Claims, 8 Drawing Sheets

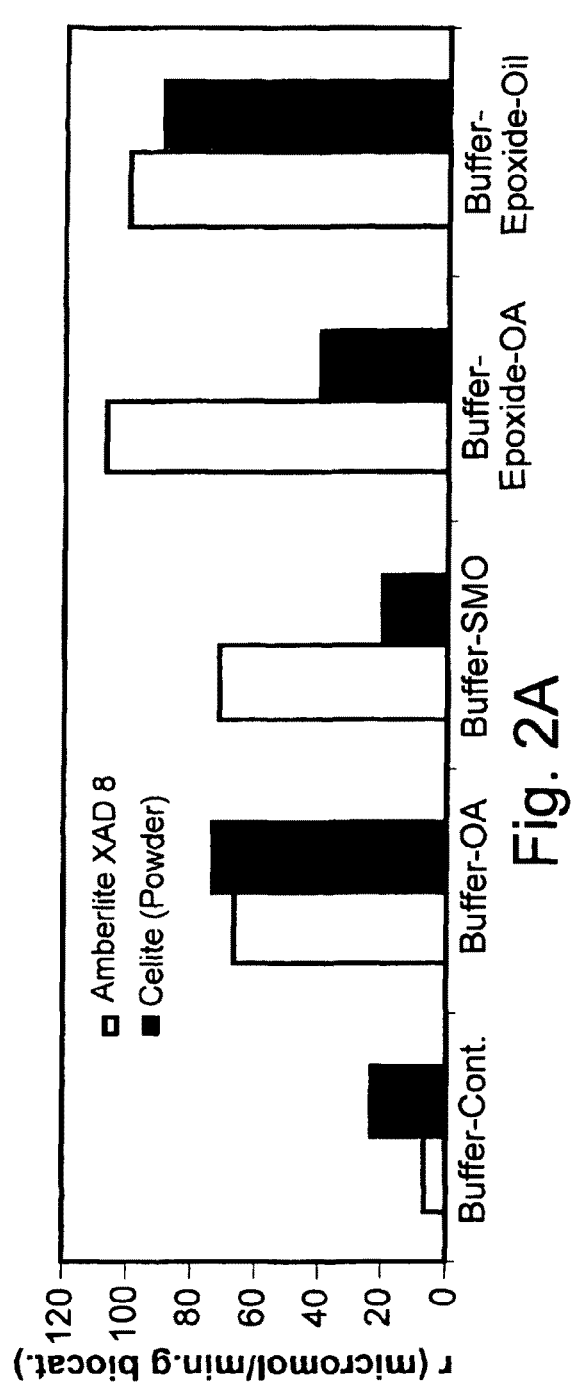
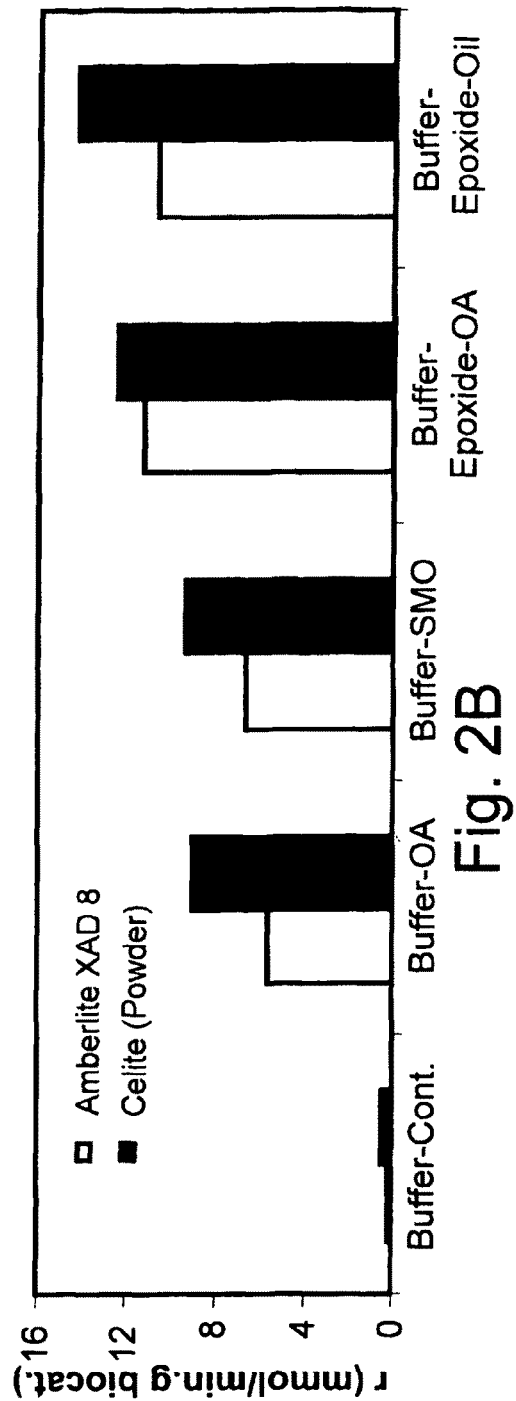

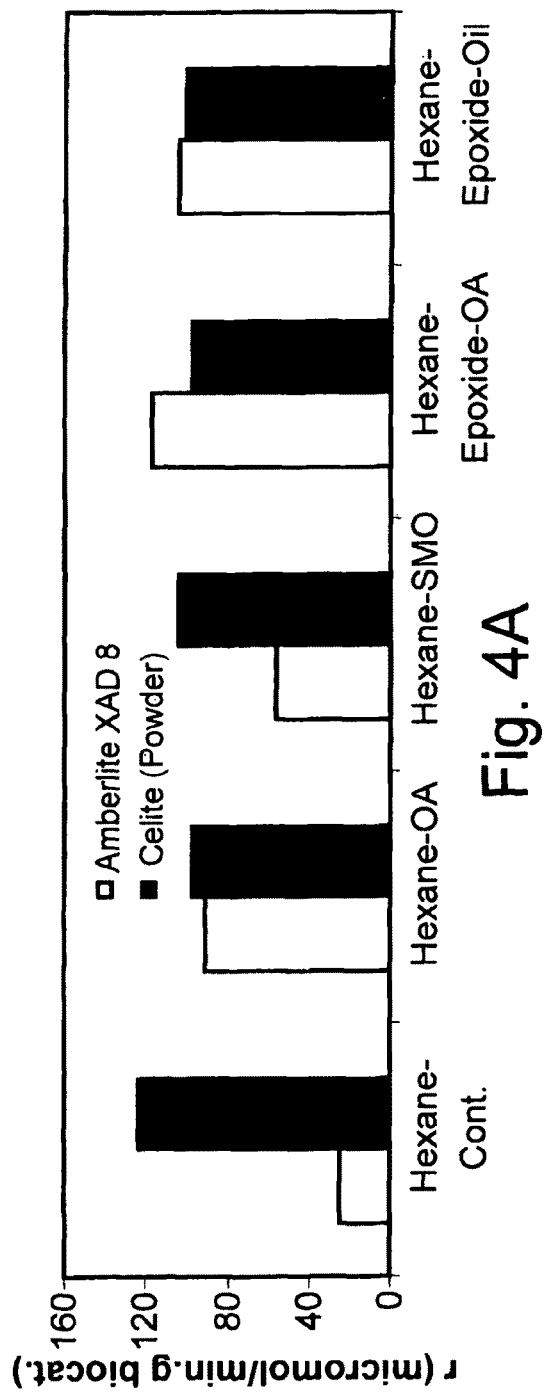
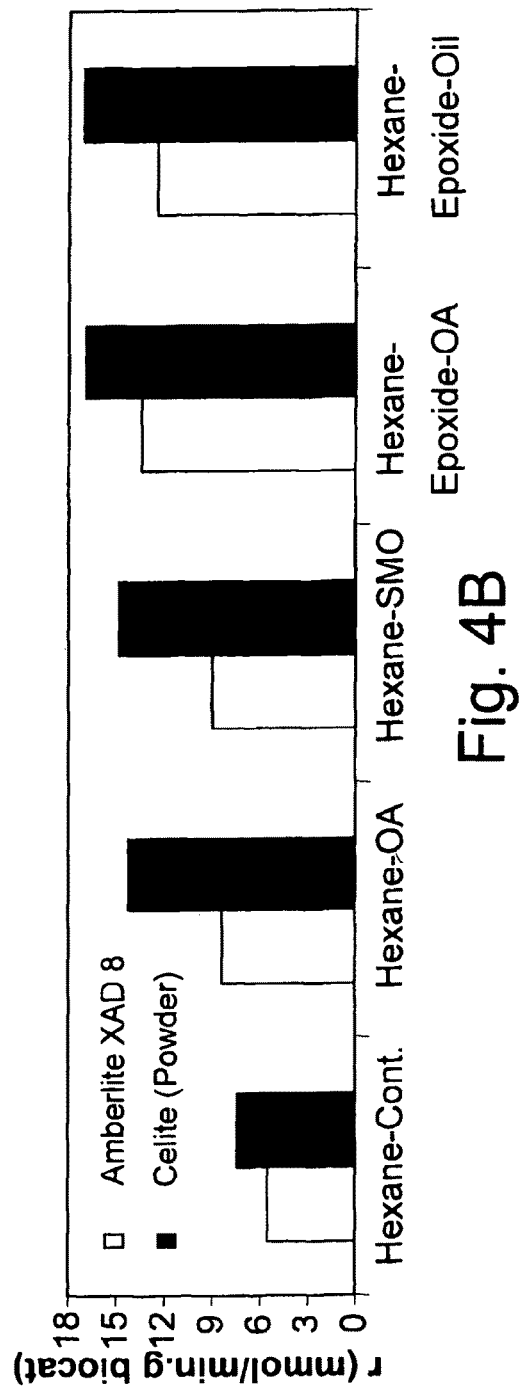
Fig. 4A
Fig. 4B

MODIFIED-IMMOBILIZED ENZYMES OF HIGH TOLERANCE TO HYDROPHILIC SUBSTRATES IN ORGANIC MEDIA

CROSS REFERENCE TO RELATED APPLICATIONS

This application is a 371 National Phase Entry Application of International Application No. PCT/IL2008/000631 filed May 7, 2008, which designated the U.S., and which claims the benefit of priority under 35 U.S.C. §119(a) of Israeli Application No. 183084 filed May 9, 2007, the contents of which are incorporated herein by reference.

FIELD OF THE INVENTION

The invention relates to immobilized interfacial enzymes, particularly lipases and phospholipases, as well as other hydrolases, having improved activity and stability towards alcohols, in particular short-chain alcohols, as well as other hydrophilic substances. The invention also relates to processes for the preparation of such enzymes, and their various industrial and investigational uses, particularly for the production of fatty acid short-chain alkyl esters, such as methyl esters, typically used as biodiesel.

BACKGROUND OF THE INVENTION

Interfacial enzymes are a class of enzymes that comprise two domains in their proteinous structure; the first is a hydrophilic domain, while the second is a hydrophobic domain. This unique feature imparts this class of enzymes to favor the interfacial area once present in a two-phase system. Under these conditions, the active conformation is formed where the hydrophilic domain of the enzyme molecules faces the aqueous layer while the hydrophobic domain faces the hydrophobic layer.

Lipases and phospholipases are the most familiar interfacial enzymes that express their catalytic activity once present in an interfacial system. Lipases (triacylglycerol hydrolase E.C. 3.1.1.3) are defined as hydrolytic enzymes that act on the ester linkage in triacylglycerol in aqueous systems to yield free fatty acids, partial glycerides and glycerol. Phospholipases also belong to the class of hydrolytic enzymes, however they cleave favorably and specifically the ester linkage of phospholipids present in aqueous systems, to yield free fatty acids, lysophospholipids, glycerophospholipids, phosphatidic acid and free alcohol, depending on the type of phospholipase.

Lipases and phospholipases are widely distributed among animals, plants and microorganisms. The interest in the industrial application of lipases and phospholipases has been rapidly growing during the last two decades. It has been found that under low water activity this class of enzymes catalyzes their reverse hydrolysis reaction. The reverse catalytic activity of lipases and phospholipases has been widely exploited for the synthesis of valuable compounds that contain ester and amide linkages or other related chemicals containing functional groups such as hydroxyl, carboxylic and amino groups. In particular, lipases and phospholipases have been utilized for reforming fats, oils, waxes, phospholipids and sphingolipids to obtain new desired functional properties, and for separating optically active compounds from their racemic mixtures. Of particular interest is the use of interfacial enzymes for the synthesis of short-chain alkyl esters (biodiesel), disclosed herein.

Currently, there are more than 40 different lipases and phospholipases commercially available, however only a few of them are prepared in commercial quantities. Some of the most industrially promising interfacial enzymes are derived from *Candida antarctica, Candida rugosa, Rhizomucor miehei, Pseudomonas* sp., *Rhizopus niveus, Mucor javanicus, Rhizopus oryzae, Aspergillus niger, Penicillium camernbertii, Alcaligenes* sp., *Burhholderia* sp., *Thermomyces lanuginosa, Chromobacterium viscosum*, papaya seeds, and pancreatin.

Immobilization of enzymes has been described by a vast number of techniques basically aiming at reducing the cost contribution of enzymes in the overall process, facilitating the recovery of enzymes from the products and enabling continuous operation of the process. Immobilization techniques are in general divided according to the following:
  1. Physical adsorption of enzymes to solid supports, such as silica and insoluble polymers.
  2. Adsorption on ion-exchange resins.
  3. Covalent binding of enzymes to a solid support material, such as epoxidated inorganic or polymer supports.
  4. Entrapment of enzymes in a growing polymer.
  5. Confinement of enzymes in a membrane reactor or in semi-permeable gels.
  6. Cross-linking enzyme crystals (CLECS's) or aggregates (CLEAS's).

All the aforementioned enzyme immobilization procedures are comprised of the following steps:
  1. Dissolving the enzyme in an appropriate buffer system with respect to pH, temperature, type of buffer salts and ionic strength.
  2. Adding the solid support into the enzyme solution and mixing for some time until enzyme molecules are immobilized on the solid support.
  3. Filtering off the solid support which contains the immobilized enzyme.
  4. Washing the support with an appropriate buffer to remove loosely bound enzyme molecules and then drying the solid support.

Interfacial enzymes, mostly lipases, have been immobilized following the aforementioned techniques. These offered immobilized enzyme preparations possessing low synthetic activity and/or short operational half-life time. In an attempt to increase the synthetic activity of immobilized lipases and other interfacial enzymes different activation methods have been applied. These methods include:
  1. Binding the surface functional groups of enzymes with hydrophobic residues such as fatty acids or polyethylene glycol.
  2. Coating the surface of enzymes with surfactants, such as polyol fatty acid esters.
  3. Contacting enzymes with hydrophobic supports, typically polypropylene, which have been pretreated with hydrophilic solvents, such as ethanol or iso-propanol.
  4. Adding enzyme activators, such as salt solution, glycerol, etc. at low concentration, typically below 1%, into the reaction system.

None of the above mentioned methods yielded satisfactory results with respect to activation, stabilization and cost-effectiveness of immobilized interfacial enzymes in order to carry out enzymatic reverse conversions at industrial quantities. Also, it has been reported that most enzymes, when immobilized according to the aforementioned procedure, either lose a significant portion of their synthetic activity or do not exhibit their full activity performance due to certain constraints imposed by the immobilization procedure. For example, coating lipases and phospholipases with polyol fatty acid esters encountered a serious challenge where lipase molecules were not fully coated with the activator; therefore those enzyme molecules not brought into contact with the activator, remained inactive.

Another major drawback of lipases and phospholipases is their low tolerance towards hydrophilic substrates, particularly short-chain alcohols and short-chain fatty acids (below C4). It has been observed in many research studies that short-chain alcohols and short-chain fatty acids, such as methanol and acetic acid, are responsible for detaching essential water molecules from the quaternary structure of those enzymes, leading to their denaturation and consequently loss of their catalytic activity. This drawback has prohibited the application of lipases for production of commercial quantities of fatty acid methyl esters "biodiesel" using oil triglycerides and methanol as substrates.

It is therefore an object of this invention to provide a new method for obtaining highly active and stable immobilized, interfacial enzymes, in particular lipases and phospholipases for synthetic applications. Of particular interest is the use of these enzymes for the synthesis of fatty acid short-chain alkyl esters for use as "biodiesel".

It is a further object of the present invention to provide highly active, stable, immobilized interfacial enzymes, possessing high tolerance towards short-chain alcohols, such as methanol, ethanol and glycerol, and short-chain fatty acids, such as acetic acid.

These and other objects of the invention will become apparent as the description proceeds.

SUMMARY OF THE INVENTION

The present invention relates to a modified interfacial enzyme immobilized on a solid support, wherein said enzyme is surrounded by hydrophobic microenvironment, and is thereby protected from deactivation and/or aggregation in the presence of hydrophilic agents, substrates and/or reaction products.

The modified interfacial enzyme of the invention may be protected by being coated with covalently bonded lipid groups.

The said support may be capable of binding said enzyme by adsorption or by covalent binding to functional groups. More specifically, said support may be organic or inorganic, and is preferably selected from the group consisting of inorganic support such as silica- and alumina-based supports, organic supports such as polymer-based support, wherein said support may contain active functional groups such as epoxy or aldehyde groups and ionic groups or said support is an ion exchange resin.

The said lipid epoxide may be selected from fatty acids, fatty acid alkyl esters, sugar fatty acid esters, medium- and long-chain alkyl glucosides, phospholipids, polyethylene glycol derivatives and quaternary ammonium salts.

In another embodiment, the modified interfacial enzyme of the invention is protected by being immobilized on or embedded in a hydrophobic solid support which supplies the hydrophobic micro-environment.

The enzyme may be a lipase, an esterase or a phospholipase. More specifically, the enzyme may be any one of Candida antarctica, Candida rugosa, Rhizomucor miehei, Pseudomonas sp., Rhizopus niveus, Mucor miehei, Mucor jauanicus, Rhizopus oryzae, Aspergillus niger, Penicillium camembertii, Alcaligenes sp., Burhholderia sp., Thermomyces lanuginosa, Chromobacterium viscosum, papaya seeds and pancreatin.

In a further aspect, the invention relates to a process for the preparation of a modified interfacial enzyme immobilized on an insoluble support, which is protected from deactivation and/or aggregation in the presence of hydrophilic agents, substrates and/or reaction products, comprising the steps of:
(a) providing a system comprised of an aqueous buffer solution and at least one organic solvent containing a lipid epoxide;
(b) mixing said interfacial enzyme with the bi-solvent system provided in step (a);
(c) adding said support to the mixture of step (b) and mixing;
(d) isolating from the mixture obtained in step (c) the interfacial enzyme immobilized on said support.

In one embodiment, said support is a porous support which may be organic or inorganic, preferably selected from the group consisting of porous inorganic support such as silica- or alumina-based supports, organic supports such as polymer-based support, and wherein said support may optionally contain active functional groups such as epoxy or aldehyde groups, or ionic groups.

In another embodiment, said organic solvent is selected from alkanes (such as octane), ether (such as di-isopropyl ether), alcohols (such as n-octanol), aldehydes (such as decanaldehyde) and ketones (such as 2-octanone) and any mixture thereof.

In a further embodiment, said lipid epoxide is selected from fatty acids, fatty acid methyl esters, sugar fatty acid esters, medium- and long-chain alkyl glucosides, phospholipids, polyethylene glycol derivatives and quaternary ammonium salts.

In yet another aspect, the present invention provides a process for the preparation of a modified interfacial enzyme immobilized on a solid support, wherein said enzyme is surrounded by hydrophobic microenvironment, thereby protected from deactivation and/or aggregation in the presence of hydrophilic substrates and/or reaction products, comprising the steps of:
(a) providing a bi-phase system comprised of an aqueous buffer solution and at least one organic solvent containing a lipid epoxide, particularly fatty acid epoxide or triglyceride epoxide;
(b) mixing said interfacial enzyme with the bi-phase system, with large excess of the epoxide, provided in step (a) to react the nucleophilic surface reactive groups of the enzyme, particularly the amino groups, with the epoxide group, to yield enzyme coated covalently with fatty acids or with triglycerides (FIG. 1);
(c) adding said support to the mixture of step (b) and mixing;
(d) isolating from the mixture obtained in step (c) the lipid-interfacial enzyme complex immobilized on said support.

Prior to mixing with the enzyme biphasic solution, said support is optionally washed to remove salts and organic materials.

In this process of the invention, the insoluble support is capable of binding the interfacial enzyme by physical adsorption or by covalent binding to functional groups. The support is preferably a porous support which may be organic or inorganic, preferably selected from the group consisting of porous inorganic support such as silica- or alumina-based supports, organic supports such as polymer-based supports, wherein said support may optionally contain active functional groups such as epoxy or aldehyde groups, or ionic groups.

The organic solvent used in step (a) of the epoxidation process of the invention, said may be, but is not limited to, an alkane (such as octane), alcohol (such as n-octanol), aldehyde (such as decanaldehyde), ether (such as di-iso-propyl ether) or ketone (such as 2-octanone) and any mixture thereof.

The interfacial enzyme to be prepared by the process of the invention is preferably a lipase, an esterase or a phospholipase. Specific non-limiting examples are enzymes derived from *Candida antarctica, Candida rugosa, Rhizomucor miehei, Pseudomonas* sp., *Rhizopus niveus, Mucor javanicus, Mucor miehei, Rhizopus oryzae, Aspergillus niger, Penicillium camembertii, Alcaligenes* sp., *Burkholderia* sp., *Thermomyces lanuginosa, Chromobacterium viscosum*, papaya seeds and pancreatin.

The interfacial enzyme of the invention, immobilized on a solid porous support, is locked at its active confirmation and is modified by being coated covalently with a large number of molecules of said lipid (bound to a surface functional group of the enzyme via their original epoxy group) and is characterized by high tolerance towards hydrophilic substrates, such as short-chain alcohols and short-chain fatty acids.

The support used in the epoxidation process of the invention is capable of binding said lipid-coated enzyme by physical adsorption or by covalent binding to functional groups, and may be organic or inorganic support, preferably selected from inorganic supports such as silica- and alumina-based supports, organic supports such as polymer-based support, and the support may contain active functional groups such as epoxy or aldehyde groups and ionic groups, or said support may be an ion exchange resin.

In this lipid coated enzyme preparation of the invention, the lipid is preferably, but not limited to, free fatty acid or fatty acid alky ester epoxide, a sugar fatty acid ester epoxide, a medium- and long-chain alkyl glucoside, a phospholipid epoxide, a polyethylene glycol epoxide derivative or a quaternary ammonium salt epoxide. Epoxides of the unsaturated lipid substrates are typically obtained by oxidizing at least one of the double bonds to an epoxide group by chemical or bio-chemical catalysis, for example by a lipase in the presence of hydrogen hyperoxide.

In another embodiment the invention relates to a process for preparing a modified interfacial enzyme immobilized on a solid support, wherein said enzyme is surrounded by hydrophobic microenvironment, thereby protected from deactivation and/or aggregation in the presence of hydrophilic substrates and/or reaction products, comprising the steps of (a) providing a system comprised of (i) an aqueous buffer or (ii) a bi-phase system comprised of an aqueous buffer and an organic solvent, (b) adding to any of said systems (i) or (ii) a hydrophobic polymeric support; (c) adding to a mixture obtained in step (b) said interfacial enzyme and mixing; and (d) isolating from the mixture obtained in step (c) the interfacial enzyme immobilized on said hydrophobic support.

In this process, the said organic solvent may be, but is not limited to n-octane, iso-octane, n-hexane, n-octanol di-isopropyl ether and oil triglycerides. The hydrophobic polymeric support may be, but is not limited to a hydrophobic aliphatic and acrylic cross-linked polymer or a hydrophobic aromatic cross-linked polymer, such as Amberlite® XAD 7HP and Amberlite® XAD 1600, respectively.

In all processes of the invention, the enzyme may be a lipase, an esterase or a phospholipase, for example *Candida antarctica, Candida rugosa, Rhizomucor miehei, Mucor miehei, Pseudomonas* sp., *Rhizopus niveus, Mucor javanicus, Rhizopus oryzae, Aspergillus niger, Penicillium camembertii, Alcaligenes* sp., *Burkholderia* sp., *Thermomyces lanuginosa, Chromobacterium viscosum*, papaya seeds and pancreatin.

The modified-immobilized hydrophobicized enzymes of the invention, or prepared by the process of the invention, may be advantageously used in the production of fatty acid alkyl esters for use as biodiesel or as intermediates for the preparation of surface-active ingredients.

Thus, an enzymatic process for the preparation of structured lipids comprising the step of reacting a fatty acid source, such as free fatty acid, triglyceride, fatty acid esters, partial glycerides, phospholipids or other fatty acid derivatives with an alcohol, such as methanol in the presence of a modified-immobilized enzyme of the invention or prepared by the process of the invention, is provided herein.

In yet another embodiment, the invention relates to a process for the preparation of short-chain alkyl esters of fatty acids, preferably fatty acid methyl esters (biodiesel) comprising stepwise adding methanol to source of fatty acids obtained from a plant, animal, algal or fish oil or a mixture of at least two of these oils that contain a lipase in accordance with the invention or prepared by a process of the invention, and allowing the reaction to proceed under suitable conditions, until said fatty acyl groups or fatty acids are converted to fatty acid methyl esters. In this process, the plant oil may be, but is not limited to soybean oil, canola oil, rapeseed oil, olive oil, castor oil, palm oil, sunflower oil, peanut oil, cotton seed oil, Jatropha oil, waste cooking oil or any oil triglycerides derived from inedible plant sources.

The invention will be described in more detail on hand of the following figures.

BRIEF DESCRIPTION OF THE FIGURES

FIG. 2A: Hydrolytic activity of immobilized *Mucor miehei* (*M. miehei*) lipase of the invention, compared with the hydrolytic activity of the same enzyme, immobilized and surfactant or lipid non-covalently coated, in a buffer solution.

FIG. 2B: Synthetic activity of immobilized *M. miehei* lipase of the invention, compared with the hydrolytic activity of the same enzyme, immobilized and surfactant or lipid non-covalently coated, in a buffer solution.

FIG. 4A: Hydrolytic activity of immobilized *M. miehei* lipase of the invention, compared with the hydrolytic activity of the same enzyme, immobilized and surfactant or lipid non-covalently coated, in n-hexane.

FIG. 4B: Synthetic activity of immobilized *M. miehei* lipase of the invention, compared with the hydrolytic activity of the same enzyme, immobilized and surfactant or lipid non-covalently coated, in n-hexane.

DETAILED DESCRIPTION OF THE INVENTION

In search for a new highly active and stable immobilized interfacial enzymes, in particular lipases and phospholipases, of high tolerance towards hydrophilic substrates, such as short-chain alcohols and short-chain fatty acids, the present inventor found that a hydrophobic microenvironment of transesterification reaction medium in the vicinity of the active-site of the enzyme, may serve as means for enhancing the activity of lipases and for increasing their resistance to hydrophilic short-chain alcohols and acids, as well as other hydrophilic agents which may be present in the reaction mixture.

The inventor thus developed different enzyme preparations, in which the enzyme is immobilized on an insoluble matrix, and is rendered hydrophobic. The enzyme may be rendered hydrophobic either directly, as shown below, for example by attachment of lipophilic residues, e.g. by epoxidation with lipid epoxides, or by being immobilized onto a hydrophobic matrix, which supplies the hydrophobic microenvironment by which the enzyme is surrounded, or in which the enzyme is embedded. It is demonstrated in this work that a hydrophobic micro-environment in the vicinity of the enzyme's active-site acts as a buffer region which is capable of protecting the enzyme from exposure to inhibiting concentrations of substrates and products having hydrophilic moieties. The hydrophobic micro-environment provided for the enzyme is responsible for controlling the access of non-inhibiting concentration ranges of short-chain alcohols to the enzyme's active-site, and also responsible for the removal of the hydrophilic reaction products formed in the vicinity of the active-site of the enzyme into the reaction medium.

Figure 1:
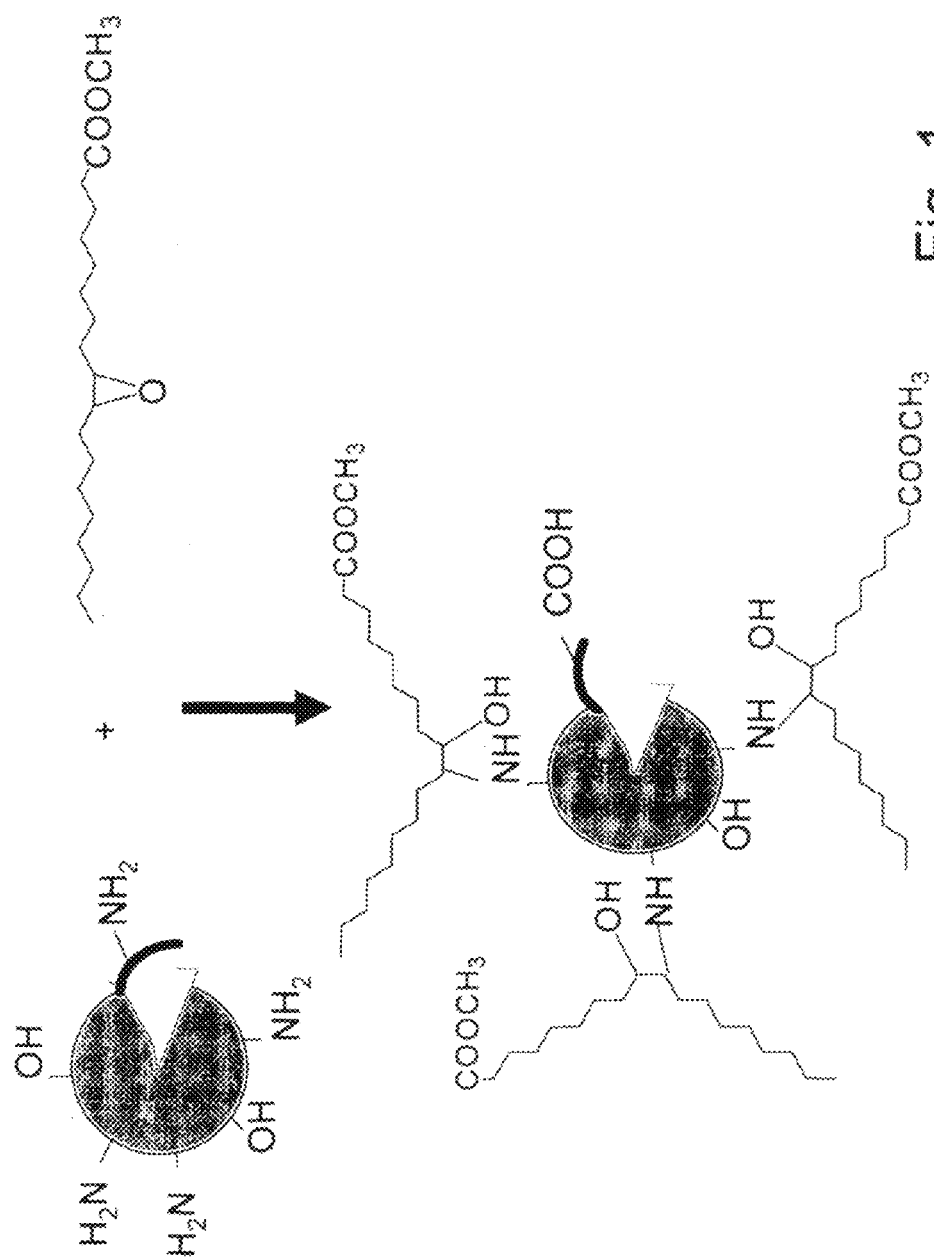
FIG. 1: A schematic illustration of the process for covalent coating of enzyme with fatty acid epoxides.

Thus, according to one aspect of the invention, the hydrophobic immobilized enzyme may be prepared by a two-step technique, substantially as follows:

Step 1: Forcing all interfacial enzyme molecules to adopt their active confirmation by reacting them with a lipid epoxide in a bi-phase system comprised of aqueous phase and an organic phase containing the lipid epoxide (see FIG. 1). The lipid epoxide is present in large excess, and thus each enzyme molecule is covalently coated with a large number of lipid molecules.

Step 2: Adding a suitable support into the bi-phase system which already contains the covalently coated enzyme.

Under these conditions, the enzyme molecules covalently coated with lipid residues or complexes that are positioned at the bi-phase interface, can be readily immobilized onto the support by simple physical adsorption, covalent binding with activated resins containing functional groups such as epoxy or aldehyde groups, or by adsorption on ion-exchange resins.

This two-step technique is employed in the preparation of active modified-immobilized interfacial enzyme in accordance with the invention.

In accordance with this aspect, the invention relates to a process for preparing stable, highly active modified-immobilized interfacial enzymes, particularly lipases, esterases and phospholipases, in which a bi-phase system comprised of an aqueous buffer solution and at least one organic solvent containing a lipid epoxide is provided; the interfacial enzyme is mixed with a large excess of the bi-phase system; a solid support is added to the mixture; and the covalently lipid-coated interfacial enzyme immobilized on the support is isolated.

The solid support is preferably a porous support which may be organic or inorganic, particularly selected from the group consisting of porous inorganic supports such as silica- or alumina-based supports, organic supports such as polymer-based support, wherein said support may optionally contain active functional groups such as epoxy or aldehyde groups, or ionic groups. Some specific supports are given in the Examples below, particularly in Table 1.

The bi-phasic system is prepared from a suitable aqueous buffer and an organic solvent. This organic solvent may be, but is not limited to, an alkane (such as octane), an ether (such as di-iso-propyl ether), an alcohol (such as n-octanol), an aldehyde (such as decanaldehyde), a ketone (such as 2-octanone) and any mixture thereof.

The immobilized enzyme of the invention, or prepared by the above epoxidation method of the invention, is very active, and particularly stable and of high tolerance to hydrophilic substrates, such as short-chain alcohols and short-chain fatty acids. Activity of about 90% is retained after even 10 cycles of reaction. This stability is of major economic importance.

In another aspect, the invention relates to an alternative method for lipase hydrophobization, avoiding the need for epoxidation and coating the enzyme with lipid moieties. Physically attached immobilized enzymes with hydrophobic micro-environment were produced by contacting hydrophobic porous polymeric matrices with a water solution or with a water-organic solvent bi-layer [also termed bi-phase] system containing different lipases. The immobilized enzymes so produced were tested in a transesterification reaction between oil triglycerides and methanol, for the production of biodiesel and glycerol, which transesterification reaction was used as a reaction model in this work. Without being bound by theory, it is suggested that the hydrophobic nature of the micro-environment is responsible for lowering the concentrations of the hydrophilic substances in the vicinity of the enzyme molecules. These hydrophilic substances may be either substrate/s used in the reaction, or the products formed by the reaction. Such a "hydrophobicized" biocatalyst ensures controlled concentrations of the hydrophilic short-chain alcohols and acids reactants which reach the enzyme vicinity, and/or fast removal of any hydrophilic substances formed in the vicinity of the enzyme molecules. As a major result the enzyme molecules are protected from the hydrophilic substrates and products by controlling the concentrations of reactants which reach the vicinity of the immobilized enzyme, as well as the fast removal of hydrophilic products once formed by the reaction. This suggestion was tested with four different lipases, each separately immobilized on four supports which differ with respect to their hydrophobicity, as shown in Example 5.

In a further embodiment, the invention relates to a process for the preparation of fatty acids short-chain alkyl esters, in particularly fatty acid methyl esters (biodiesel). Generally, in this process, methanol is first added stepwise to a source of fatty acids, such as a plant, animal, algal, fish oil or any oil derived from fungi, or a mixture of at least two of these oils. A modified lipase immobilized on a solid support which is covalently covered with a lipid, as prepared for example by the process of the invention, or a lipase immobilized on a hydrophobic matrix in accordance with the invention, is added to the methanol/fatty acid source mixture, and the reaction is allowed to proceed until the fatty acid source is converted to fatty acid methyl esters.

Within the context of the present application, the terms support, matrix, adsorbent are used synonymously and may be interchanged.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the intended scope of the invention.

EXAMPLES

Example 1

Preparation of Immobilized Lipase (Lipozyme TL)

Lipase derived from *Thermomyces lanuginosa* (1 ml of Lipozyme TL 100L, Novozymes, Denmark) was mixed in a bisolvent system comprised of 1 ml phosphate buffer of 0.05 M and pH 6.5, and 10 ml of n-hexane containing a lipid epoxide. The mixture was stirred for 48 hours. A support (1 g) was added into the system and the mixture was stirred for 8 hours. The support containing the modified-immobilized enzyme was filtered off and dried in a desiccator overnight to yield the highly active covalently lipid-coated-immobilized lipase.

Table 1 shows the relative transesterification activity of Lipozyme TL 100L immobilized on different supports. Reactions were carried out by adding immobilized lipase (0.2 g) to soybean oil (2.5 g) and methyl alcohol (0.3 g). The reaction system is mixed magnetically or by shaking at 30° C. The reaction rate is determined by measuring the fatty acid methyl esters produced after 1 hour under the above mentioned conditions

TABLE 1

The reaction rate using different fatty acid epoxide-modified Lipozyme for the transesterifcation of soybean oil triglycerides to obtain fatty acid methyl esters (FAME). Reaction conditions: olive oil (2.5 g) and methanol (0.2 g) are mixed with lipase TL 100 L modified-immobilized on different supports (0.2 g) for 1 hour. The reaction mixture is shaken at 300 rpm and at 30° C.

| Type of support | Reaction rate (micromol FAME/min · g biocatalyst) |
|---|---|
| Amberlite XAD 4 (Rohm&Haas, USA) | 16 |
| Amberlite XAD 16 (Rohm&Haas) | 12 |
| Amberlite XAD 7HP (Rohm&Haas) | 10 |
| Amberlite XAD 16HP (Rohm&Haas) | 22 |
| Duolite XAD 761 (Rohm&Haas) | 11 |
| Amberlite XAD 1180 (Rohm&Haas) | 9 |
| Amberlite XAD 1600 (Rohm&Haas) | 8 |
| Duolite A7 (Rohm&Haas) | 12 |
| Duolite A561 (Rohm&Haas) | 10 |
| Duolite A568 (Rohm&Haas) | 12 |
| Duolite C467 (Rohm&Haas) | 6 |
| Amberlyst A-21 (Rohm&Haas) | 10 |
| Dowex monosphere 77 (DOW, USA) | 13 |
| Dowex optipore L493 (DOW, USA) | 12 |
| Dow styrene DVB (DOW, USA) | 18 |
| MTO Dowex optipore SD-2 (DOW, USA) | 10 |
| Dowex MAC-3 | 9 |
| Amberlite FPA53 (Rohm&Haas) | 11 |
| Amberlite FPC22H (Rohm&Haas) | 10 |
| Amberlite FPA4OCl (Rohm&Haas) | 2 |
| AmberliteIRC50 (Rohm&Haas) | 7 |
| Purolire A109 (Purolite, USA) | 12 |

Example 2

Preparation of Immobilized Lipase

The immobilization procedure of Example 1 was repeated using different lipases (100 mg) and using triglycerides epoxides. Reaction rates for production of fatty acid methyl esters under the above described conditions are described in Table 2.

TABLE 2

The reaction rate using different fatty acid epoxide-modified lipases for the transesterifcation of soybeans oil triglycerides to obtain fatty acid methyl esters (FAME). Reaction conditions: Soybean oil (2.5 g) and methanol (0.3 g) are mixed with different lipases coated covalently with triglycerides epoxides and immobilized on Amberlite XAD 4 (0.2 g) for 1 hour. The reaction mixture is shaken at 300 rpm and at 30° C.

| Type of support | Reaction rate (micromol FAME/min · g biocat.) |
|---|---|
| *Candida antarctica* | 9.6 |
| *Candida rugosa* | 7.7 |
| *Rhizomucor miehei* | 12.5 |
| *Pseudomonas cepacia* | 16.2 |
| *Penicillium camembertii* | 4.2 |
| *Alcaligenes* sp. | 12.3 |
| *Rhizopus niveus* | 3.4 |
| *Mucor javanicus* | 12.3 |
| *Rhizopus oryzae* | 14.2 |
| *Aspergillus niger* | 6.3 |
| *Burkholderia* sp. | 12.1 |
| *Thermomyces lanuginosa* | 17.1 |
| *Chromobacterium viscosum* | 15.1 |

Example 3

Immobilized Lipases for the Preparation of Fatty Acid Methyl Esters (Biodiesel)

Immobilized modified *M. miehei* lipase preparations were prepared according to the procedure of Example 1, using Amberlite XAD 8 or Celite (powder) as support, and Buffer (control) n-hexane or acetone (Ac) as the organic solvent.

These preparations were used for the preparation of fatty acid methyl esters (biodiesel). The reaction is initiated by adding immobilized lipase (100 mg) and shaking the reaction medium at 30° C. for 6 hours.

The hydrolytic and synthetic activities of the different enzyme preparations [Buffer-Epoxide-OA in which the enzyme is covalently coated with oleic acid, and Buffer-Epoxide-Oil, in which the enzyme is covalently coated with an oil (triglyceride, e.g. triolein)] were compared with those of other enzyme preparation (that are not covalently coated with a lipid): Buffer (control) in which the enzyme is simply immobilized on the support; Buffer-Oleic acid (Buffer-OA) in which the support-immobilized enzyme is coated with the fatty acid; Buffer-SMO, in which the support-immobilized enzyme is coated with sorbitan monostearate.

Figure 3A:
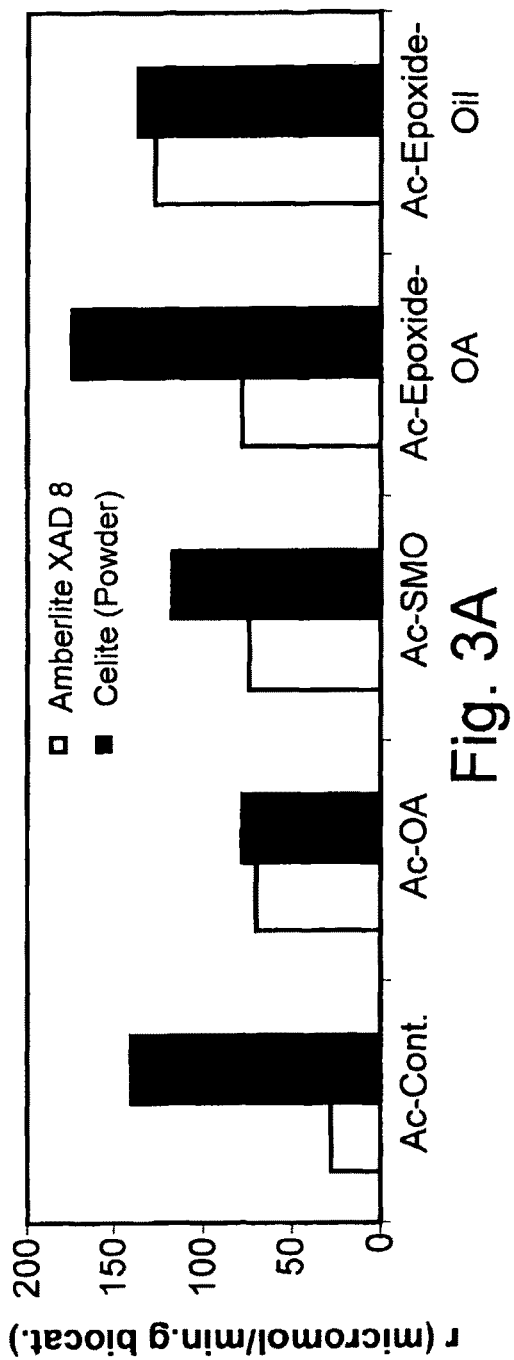
FIG. 3A: Hydrolytic activity of immobilized *M. miehei* lipase of the invention, compared with the hydrolytic activity of the same enzyme, immobilized and surfactant or lipid non-covalently coated, in acetone.
Figure 3B:
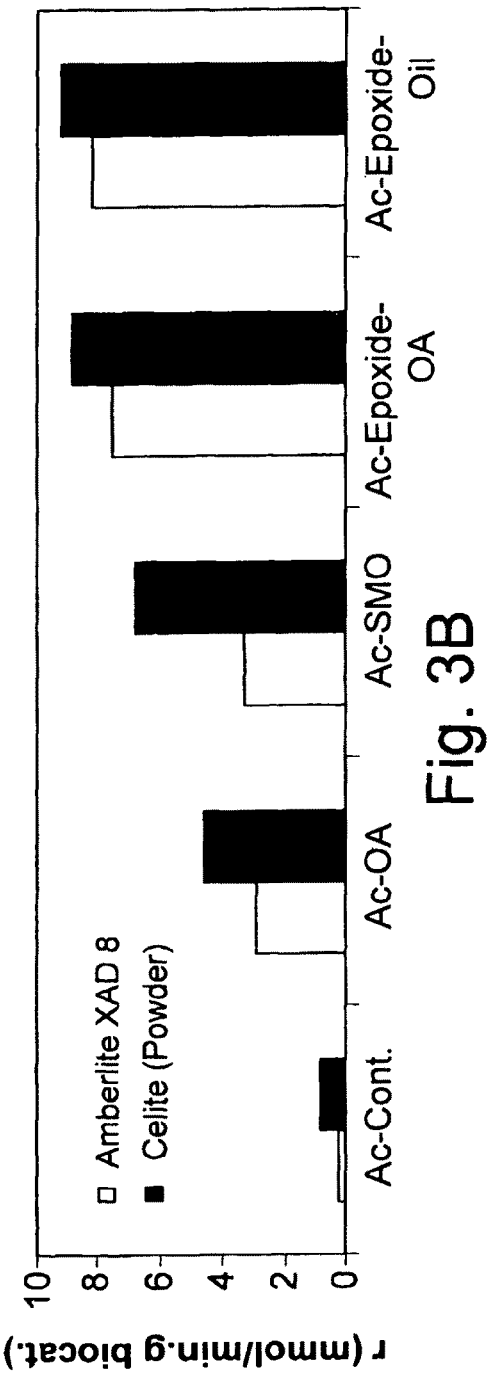
FIG. 3B: Synthetic activity of immobilized *M. miehei* lipase of the invention, compared with the hydrolytic activity of the same enzyme, immobilized and surfactant or lipid non-covalently coated, in acetone.
Figure 5:
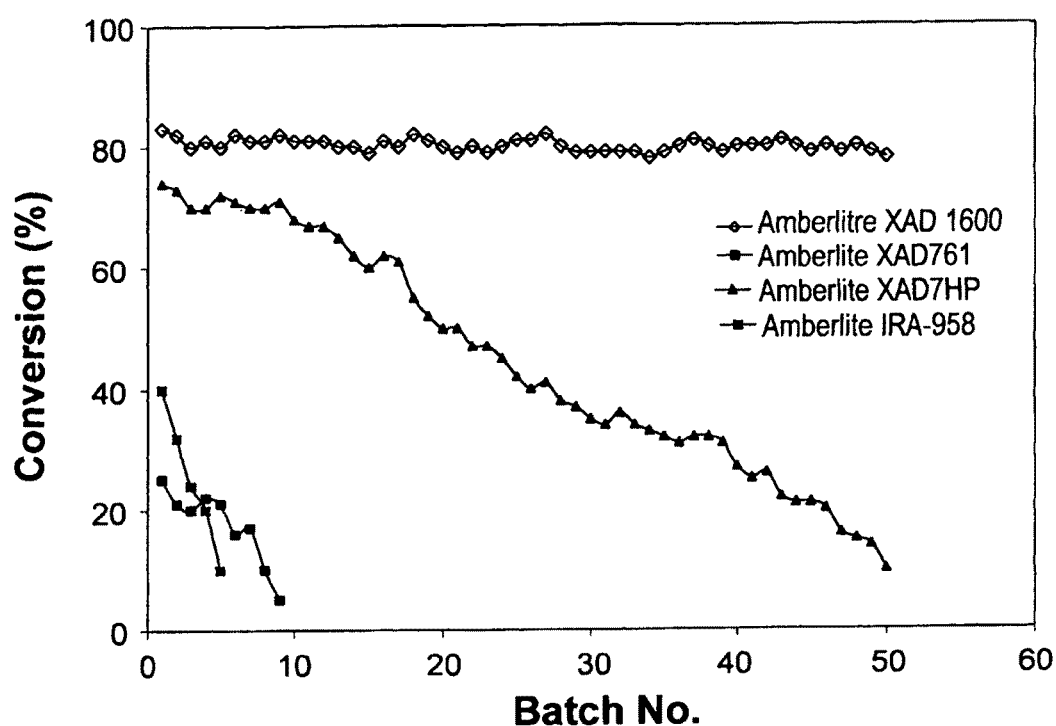
FIG. 5: The reaction conversion (%) into fatty acid methyl esters using *Thermomyces lanuginose* lipase immobilized on various matrices using the same batch of biocatalyst in consecutive transesterification reactions. Reaction conditions: soybean oil (2.5 g), methanol (0.3 g added in three portions one hour apart) and immobilized lipase (250 mg) were mixed in thermostated shaker at 30° C. for 4 hours.
Figure 6:
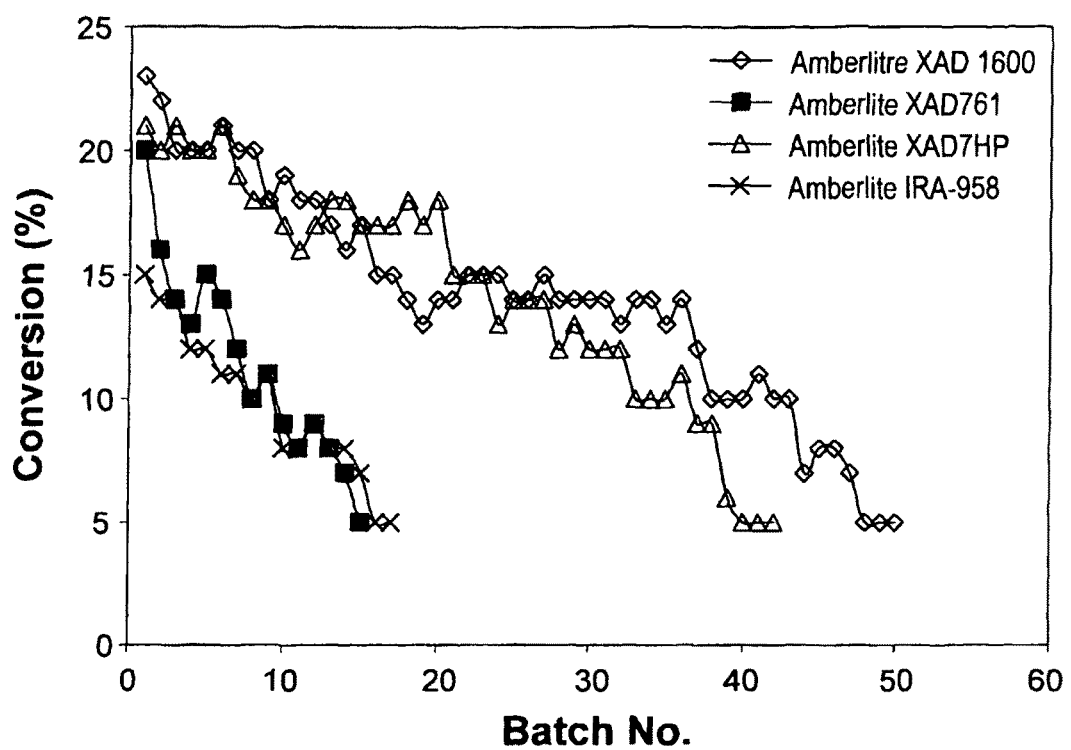
FIG. 6: The reaction conversion (%) into fatty acid methyl esters using *Candida antarctica* B lipase immobilized on various matrices using the same batch of biocatalyst in consecutive transesterification reactions. Reaction conditions were as in FIG. 5.
Figure 7:
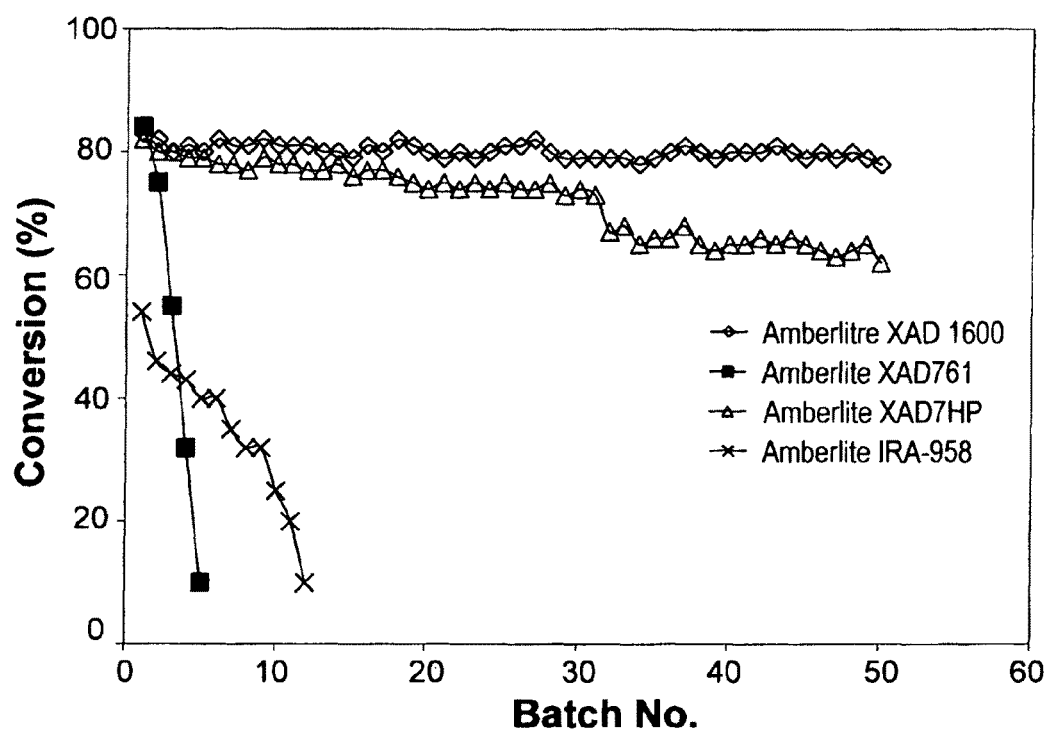
FIG. 7: The reaction conversion (%) into fatty acid methyl esters using *Pseudomonas cepacia* lipase immobilized on various matrices using the same batch of biocatalyst in consecutive transesterification reactions. Reaction conditions were as in FIG. 5.
Figure 8:
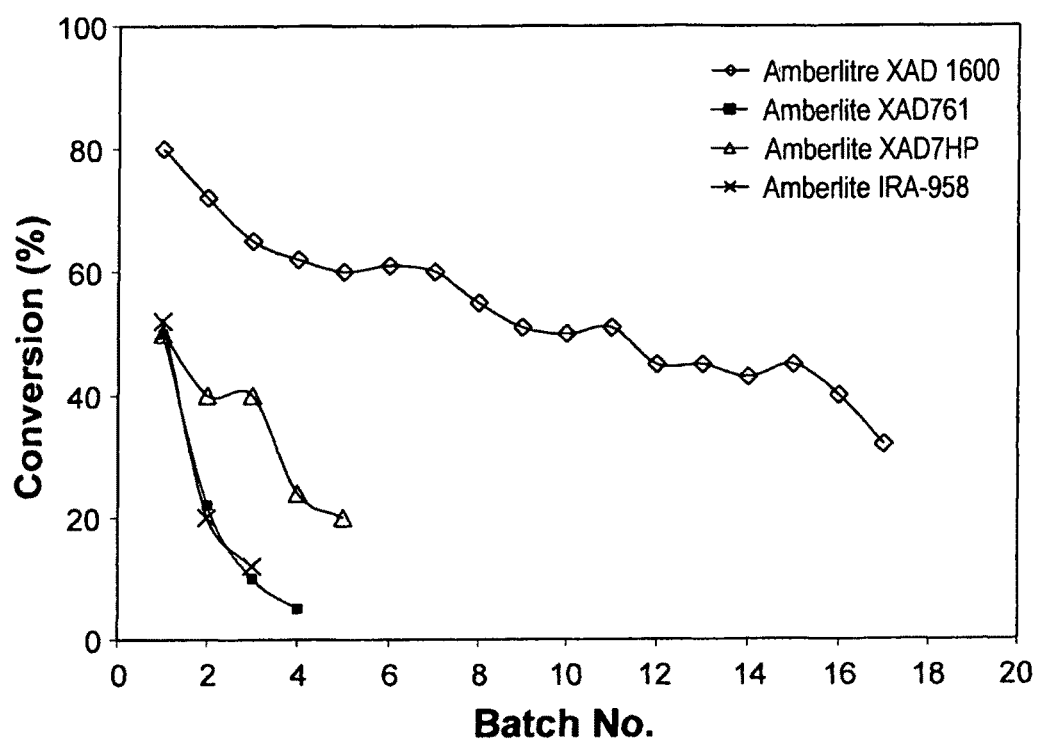
FIG. 8: The reaction conversion (%) into fatty acid methyl esters using *Alcaligenes* sp. lipase immobilized on various matrices using the same batch of biocatalyst in consecutive transesterification reactions. Reaction conditions were as in FIG. 5.

The results are shown in FIGS. 2 to 4. As can be seen, both the hydrolytic and synthetic activities of the enzymes of the invention, which are covalently coated with a lipid component, were considerably and significantly higher than those of the other enzyme preparations.

In addition, most of the activity of the enzyme is retained even after 10 and more cycles of reaction (data not shown).

The epoxide-modified enzyme preparations of the invention thus exhibit high activity and increased stability.

Example 4

Immobilization of Lipases in Buffer or Bi-Phase Systems

Lipase (3000 units of *Thermomyces lanuginose* lipase, *Candida antarctica* lipase B, both from Novozymes, Denmark, *Pseudomonas cepacia* lipase, Amano Enzyme Inc., Japan, or *Alcaligenes* sp. lipase, Meito Sangyo, Japan) was mixed in a buffer solution (10 ml, pH=7) containing a polymeric support (1 g) at room temperature for 8 hours. The immobilized enzyme was filtered off and dried over silica in a desiccator. The same procedure can be carried out in a bi-phase system comprised of similar volumes of a buffer solution and an organic solvent, for example iso-octane.

The following supports all manufactured by Rohm & Haas, USA, were used:
 Amberlite XAD 1600, defined as hydrophobic adsorbent;
 Amberlite XAD761, defined as hydrophilic adsorbent;
 Amberlite XAD7HP defined as polar and non-polar adsorbent; and
 Amberlite IRA-958 defined as a polar anion exchange resin.

Example 5

Use of the Immobilized Lipases of Example 4 in the Production of Biodiesel

The activity of the immobilized lipases prepared in Example 4 was evaluated using the transesterification of oil triglycerides and methanol for the production of biodiesel and glycerol as a by-product. Reactions were initiated by the addition of 10% w/w immobilized lipase into magnetically stirred soybean oil (2.5 g) containing methanol (0.3 g added in three portions one hour apart over 4 hours).

The conversion (%) of the oil into fatty acid methyl esters for the different lipases immobilized on various matrices, using the same batch of biocatalyst while exchanging the reaction medium after 4 hours, is shown in FIGS. 5-8. Lipases immobilized on a hydrophobic support (adsorbent) such as Amberlite® XAD 1600 maintained their transesterification activity in repeated use for a much higher number of batches compared to other similar enzymes, however immobilized on other types of supports. Also, it can be clearly seen that for this type of reaction, all lipases immobilized on hydrophilic supports exhibited poor transesterification activity as well as poor repeated use in consecutive batches. It has been noticed that lipases immobilized on hydrophilic supports like Amberlite® XAD761 and Amberlite® IRA-958 formed aggregates of biocatalysts saturated with the formed hydrophilic product of the reaction, namely glycerol. Due to the accumulation of the formed product and also because of the high concentration of methanol in the vicinity of the immobilized enzyme, the biocatalysts exhibited poor activity as well as low number of repeated uses.

In contrast, lipases, especially *Thermomyces lanuginose* and *Pseudomonas cepacia* lipase, immobilized on hydrophobic supports like Amberlite® XAD 1600 and Amberlite® XAD7HP yielded higher transesterification activity and also maintained their transesterification activity in more than 50 repeated cycles using the same batch of biocatalyst.

The invention claimed is:

1. A modified active interfacial enzyme immobilized on a solid hydrophobic support, wherein said enzyme is a lipase, an esterase or a phospholipase and wherein said enzyme is coated with lipid epoxide groups that are covalently bonded to surface nucleophilic groups of said enzyme via their original epoxy group, and said modified enzyme is thereby surrounded by hydrophobic microenvironment, thereby protected from deactivation and/or aggregation in the presence of hydrophilic agents, substrates and/or reaction products.

2. The modified interfacial enzyme of claim 1, wherein said support is capable of binding said enzyme by adsorption or by covalent binding to functional groups.

3. The modified interfacial enzyme of claim 1, wherein said support is organic polymer-based support, wherein said support may contain active functional groups such as epoxy or aldehyde groups and ionic groups or said support is an ion exchange resin.

4. The modified interfacial enzyme of claim 1, wherein said lipid groups are selected from fatty acids, fatty acid alkyl esters, sugar fatty acid esters, medium- and long-chain alkyl glucosides, phospholipids and polyethylene glycol fatty acid derivatives.

5. The enzyme of claim 1, wherein said enzyme is selected from the group consisting of *Candida antarctica, Candida rugosa, Rhizomucor miehei, Pseudomonas* sp., *Rhizopus niveus, Mucor miehei, Mucor javanicus, Rhizopus oryzae, Aspergillus niger, Penicillium camembertii, Alcaligenes* sp., *Burkholderia* sp., *Thermomyces lanuginosa, Chromobacterium viscosum*, papaya seeds and pancreatin.

6. A process for the preparation of short-chain alkyl esters of fatty acids, preferably fatty acid methyl esters (biodiesel) comprising the step of: stepwise adding methanol to a plant, animal, algal or fish oil or a mixture of at least two of these oils that contains the modified lipase, esterase or phospholipase immobilized on the solid hydrophobic support of in claim 1, and allowing the reaction to proceed under suitable conditions, until said oil triglycerides are converted to fatty acid methyl esters.

7. The process of claim 6, wherein said plant oil is soybean, canola, rapeseed, olive, palm oil, sunflower oil, peanut oil, cotton seed oil, waste cooking oil or any oil triglycerides derived from inedible plant sources.

\* \* \* \* \*